United States Patent

Joseph et al.

[11] Patent Number: 5,987,969
[45] Date of Patent: Nov. 23, 1999

[54] APPARATUS AND METHOD FOR DETERMINING DYNAMIC STABILITY OF EMULSIONS

[75] Inventors: Daniel D. Joseph, Minneapolis, Minn.; Geoffrey McGrath; Gustavo Nunez, both of Caracas, Venezuela; Pedro J Ortega, Los Teques Edo Miranda, Venezuela

[73] Assignee: Intevep, S.A., Caracas, Venezuela

[21] Appl. No.: 09/030,561

[22] Filed: Feb. 25, 1998

[51] Int. Cl.$^6$ .................................................... G01N 11/00

[52] U.S. Cl. .......................................... 73/53.01; 73/54.39

[58] Field of Search .............................. 73/53.01, 54.02, 73/54.39, 61.41, 61.43, 61.44, 61.47, 53.02, 60.11

[56] References Cited

U.S. PATENT DOCUMENTS

| | | | |
|---|---|---|---|
| 4,618,348 | 10/1986 | Hayes et al. | 44/51 |
| 5,042,292 | 8/1991 | Plint et al. | 73/60 |
| 5,319,958 | 6/1994 | Date et al. | 73/53.01 |

Primary Examiner—Hezron Williams
Assistant Examiner—Thuy Vinh Tran
Attorney, Agent, or Firm—Bachman & LaPointe, P.C.

[57] ABSTRACT

An apparatus for characterizing dynamic stability of an emulsion includes a test vessel, a gap within the test vessel defined between a stationary surface and a moving surface; and an inlet for feeding an emulsion through the gap within the test vessel, whereby dynamic stability of the emulsion can be characterized based upon cycles of flow through the test vessel. Methods for characterizing dynamic stability are also disclosed.

24 Claims, 4 Drawing Sheets

APPARATUS AND METHOD FOR DETERMINING DYNAMIC STABILITY OF EMULSIONS

BACKGROUND OF THE INVENTION

The present invention relates to an apparatus and method for determining dynamic stability of an emulsion and, more particularly, to a method and apparatus for accurately and repeatably simulating flow conditions so that the dynamic stability of an emulsion can be determined at the flow conditions.

Emulsions are used in a wide variety of industries and applications. In these various industries, emulsion stability is frequently a critical product characteristic.

In the fuel industry, heavy hydrocarbon in water emulsions are used to provide a combustible fuel. One example of this type of emulsion is a bitumen in water emulsion provided by Bitor, S.A. under the trademark Orimulsions®.

No apparatus or device is currently known which can directly measure the resistance to instability of such emulsion products. In order to evaluate dynamic stability of an emulsion in a particular flow system, expensive empirical procedures must be followed which are not necessarily repeatable for different types of emulsion and/or other flow conditions.

The need remains for a method and apparatus for accurately and repeatably characterizing the dynamic stability of an emulsion.

It is therefore the primary object of the present invention to provide an apparatus for characterizing dynamic stability of an emulsion which is simple in structure and use and which provides accurate and repeatable results.

It is a further object of the present invention to provide a method for characterizing dynamic stability of an emulsion which is efficient, accurate and repeatable in providing results for various flow conditions and emulsions.

It is a still further object of the present invention to provide an apparatus and method as described above which can be calibrated so as to simulate the conditions of a particular flow environment, thereby allowing the evaluation of dynamic stability of an emulsion in a particular flow environment.

Other objects and advantages of the present invention will appear hereinbelow.

SUMMARY OF THE INVENTION

In accordance with the present invention, the foregoing objections and advantages are readily attained.

According to the invention, an apparatus is provided for characterizing dynamic stability of an emulsion, which apparatus comprises: a test vessel; means defining a gap within said test vessel between a stationary surface and a moving surface; and means for feeding an emulsion through said gap within said test vessel, whereby dynamic stability of said emulsion can be characterized based upon cycles of flow through said test vessel.

Furthermore, a method is provided for characterizing dynamic stability of an emulsion, which method comprises the steps of (a) providing an emulsion to be evaluated; (b) flowing said emulsion through a gap defined between a stationary surface and a moving surface so as to expose said emulsion to a flow field; and (c) repeating step (b) for a number of cycles selected from the group consisting of a first number of cycles sufficient to break said emulsion, and a preselected threshold second number of cycles, wherein said number of cycles is indicative of dynamic stability of said emulsion.

Still further, a method for determining dynamic stability of an emulsion in a particular flow environment is provided, which method comprises the steps of providing an emulsion; providing a gap having a width between a stationary surface and a moving surface wherein the moving surface moves substantially perpendicularly to said width; calibrating said width and movement speed of said moving surface so as to simulate flow conditions of said flow environment; flowing said emulsion through said gap so as to subject said emulsion to a flow field; and evaluating said emulsion after flow through said gap so as to determine dynamic stability of said emulsion in said flow environment.

DETAILED DESCRIPTION OF THE DRAWINGS

A detailed description of preferred embodiments of the present invention follows, with reference to the attached drawings, wherein:

FIG. 1 schematically illustrates an apparatus in accordance with the present invention;

FIG. 2 schematically illustrates a system including the apparatus in accordance with the present invention;

DETAILED DESCRIPTION

The invention relates to a method and apparatus for characterizing the dynamic stability of an emulsion, particularly of a viscous hydrocarbon in water emulsion.

Although the teachings of the present invention have applicability to a wide variety of emulsions, the description of the present invention will be made in terms of the preferred embodiment which is for use in evaluating the dynamic stability of a hydrocarbon in water emulsion, particularly a viscous hydrocarbon or bitumen in water emulsion which is suitable for use as a combustible fuel.

In accordance with the invention, an apparatus is provided for characterizing and determining the dynamic stability of an emulsion and for evaluating such dynamic stability with reference to a particular flow environment such as a particular section of a pipeline, a pump and the like.

Figure 1:
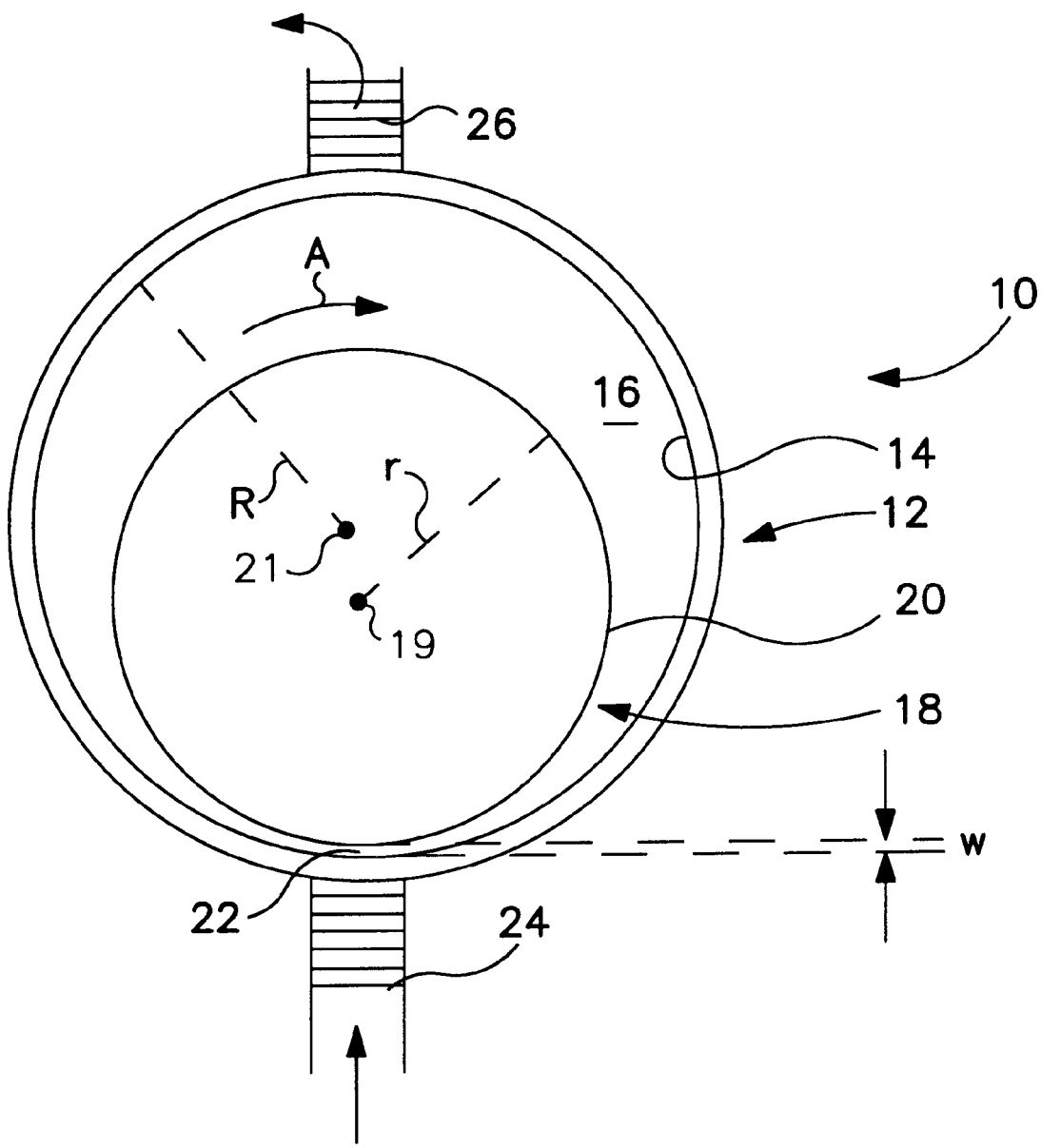

Referring to the drawings, FIG. 1 shows schematically an apparatus 10 for use in characterizing dynamic stability of an emulsion in accordance with the present invention. As shown, apparatus 10 preferably includes a test vessel such as first or external cylinder 12 having an inner surface 14 defining an inner space 16, and also includes test vessel such a second or inner cylinder 18 positioned within cylinder 12 and having an external surface 20.

As shown in FIG. 1, inner cylinder 18 is preferably positioned eccentrically with respect to cylinder 12 such that the central axis 19 of cylinder 18 is spaced from the central axis 21 of cylinder 12, and preferably parallel thereto. As shown, inner surface 14 of external cylinder 12 and external surface 20 of inner cylinder 18 define an eccentric or irregular annular area including a gap 22 having a width "w" defined between the closest portions of inner surface 14 and external surface 20.

Still referring to FIG. 1, an inlet 24 is preferably provided through the sidewall of external cylinder 12, and an outlet 26 is also preferably provided through the sidewall of external cylinder 12, such that a sample of emulsion to be tested in apparatus 10 can be passed through the annular space defined between external cylinder 12 and inner cylinder 18 from inlet 24 to outlet 26. As shown in FIG. 1, inlet 24 may preferably be positioned so as to coincide or overlap substantially with gap 22 corresponding with the minimum gap or gap width between surface 20 of inner cylinder 18 and surface 14 of external cylinder 12.

Still further in accordance with the present invention, one or the other of cylinders 12, 18 is provided rotatable around its central axis relative to the other of cylinders 12, 18 such that gap 22 is defined between a substantially fixed or static surface and a moving or rotating surface. In this regard, as will be understood with reference to the drawings, the moving surface at gap 22 is moving in a direction substantially perpendicular to the width of gap 22. As shown, cylinder 18 may be rotatable relative to cylinder 14 as illustrated by arrow A.

Figure 2:
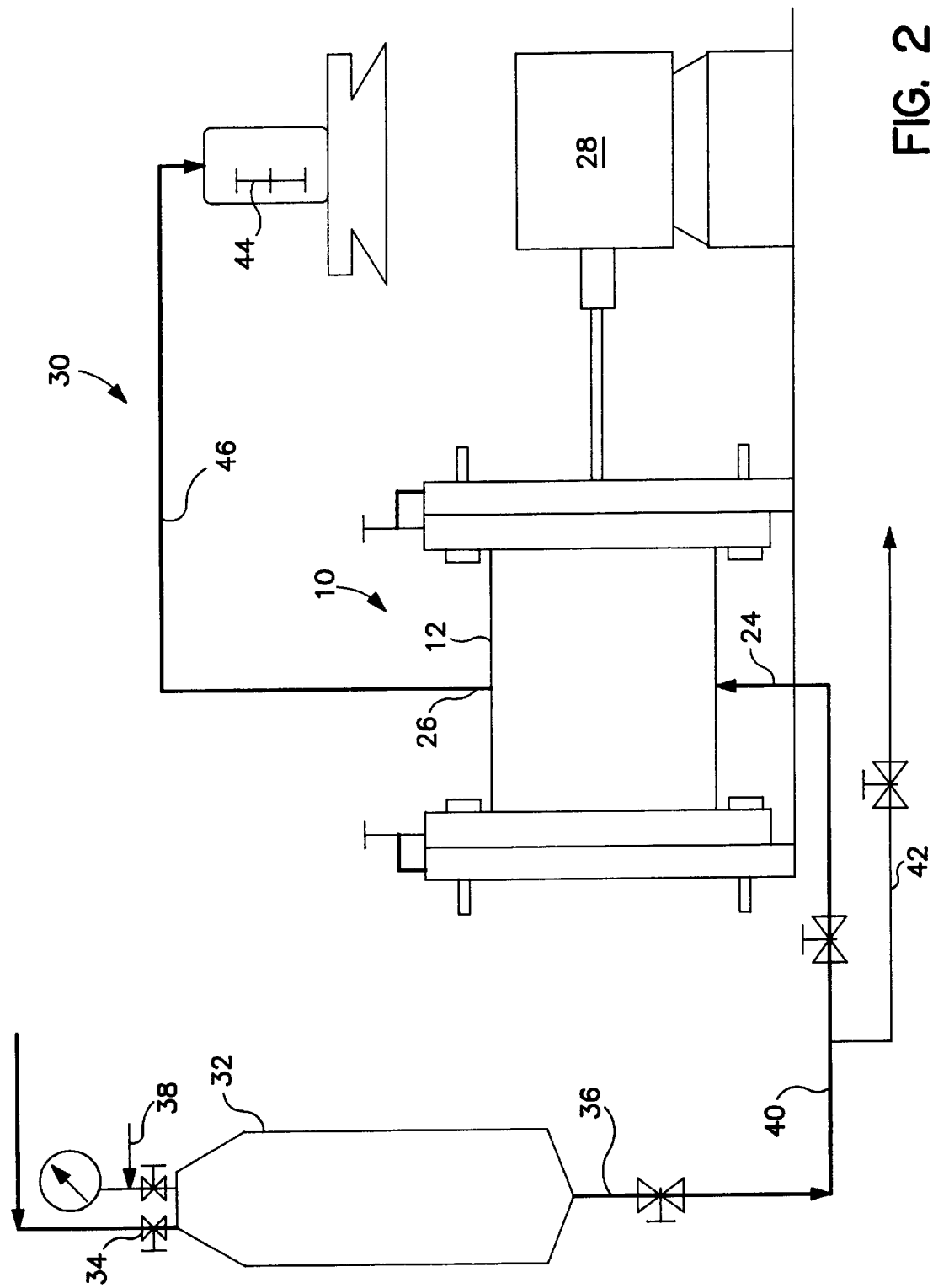

Referring also to FIG. 2, which illustrates a system 30 including apparatus 10 for carrying out the method of the present invention, it is also preferred that one or the other of cylinders 12, 18 be movable laterally with respect to axes thereof with respect to the other of cylinders 12, 18 such that the width w of gap 22 can be adjusted by relative movement of one or the other of cylinders 12, 18. As shown in FIG. 2, mechanical structure such as adjustment screws for positioning external cylinder 12 may be provided for accomplishing movement of external cylinder 12 relative to inner cylinder 18. In the embodiment of FIG. 2, inner cylinder 18 is preferably provided rotatable relative to external cylinder 12, and may further be provided with motive means such as a variable frequency motor for rotating inner cylinder 18 relative to external cylinder 12 at various desired speeds.

Still referring to FIG. 2, system 30 in accordance with the present invention preferably further includes a pressurized tank or carboy 32 having an inlet 34 for an emulsion sample, an outlet 36 for the emulsion, an inlet 38 for pressurized gas such as air or nitrogen and a line 40 flowing from outlet 36 to apparatus 10 as desired.

Also as shown in FIG. 2, a cleaning outlet for draining the liquid contained in the system during cleaning may be provided and is illustrated schematically as element 42. A holding tank 44 for receiving the emulsion being evaluated or characterized is also provided, and is connected to an outlet of apparatus 10 through line 46 as shown.

In accordance with the present invention, apparatus 10 serves to provide a gap between a substantially stationary surface and a moving surface through which an emulsion can be flowed or passed, thereby subjecting the emulsion to a flow field including a shear, a pressure gradient, or both, preferably in known quantities, so as to evaluate or characterize the dynamic stability of the emulsion. In accordance with the present invention, apparatus 10 may suitably be used to gauge a particular emulsion against a known emulsion of acceptable quality, for example by measuring the number of passes or cycles through apparatus 10 which are required to break an emulsion, and comparing this number of cycles to a number of cycles required to break the acceptable quality emulsion.

Apparatus 10 may be calibrated such that the flow field includes a shear component which may be representative of a large number of different kinds of flow conditions, and also to include a pressure gradient which may be representative of other flow conditions including certain types of pumps.

In order to generate a flow field including a pressure gradient, cylinder 18 may preferably be positioned eccentric or non-concentric relative to cylinder 12 so as to generate the desired pressure gradient, as is illustrated in FIG. 1.

Further, in accordance with another embodiment of the present invention apparatus 10 may suitably be used so as to provide a representation of emulsion-destructive conditions to be experienced in a particular flow environment such as a known pipeline, a particular pump, or the like, such that apparatus 10 can then be used to evaluate whether an emulsion will remain stable or be broken upon flowing through a particular flow environment. In this embodiment, as will be discussed below, the width of gap 22 and rotation speed of inner cylinder 18 relative to external cylinder 12 can be adjusted so as to calibrate apparatus 10 to simulate a particular flow environment.

In operation, cylinder 12 is moved relative to cylinder 18 so as to provide gap 22 of a desired width w, and cylinder 18 is rotated using motive means 28 at a desired speed of rotation so as to create a desired flow field including shear conditions and/or pressure gradient at gap 22. A sample of emulsion is then fed to carboy 32 along with pressurized gas, which carries the emulsion through line 40 to apparatus 10 wherein the emulsion is passed or flowed through gap 22 and out of apparatus 10 to holding tank 44 wherein the characteristics of the emulsion after the pass through gap 22 can be measured.

As set forth above, one use of the apparatus and method of the present invention is to gauge the dynamic stability of an emulsion against an acceptable emulsion at a particular gap width and rotation speed setting. For example, at a particular setting or calibration of cylinders 12, 18, six passes through system 30 may be required before an acceptable good quality emulsion is broken. Other emulsions can then be tested under the same conditions to determine whether the emulsion will break before six cycles through gap 22, or whether the emulsion will maintain its dynamic stability.

In accordance with a further embodiment of the present invention, apparatus 10 can be used to simulate or recreate conditions to which an emulsion is exposed during flow through a particular pipeline or other flow conduit and flow enhancing device such as a pump and the like. In this regard, an emulsion of known qualities may be passed once, or several times, through the pipeline or flow environment of interest so as to provide a subsequent, flowed emulsion which can be evaluated to determine the flow characteristics thereof. The same known emulsion can then be used to pass through apparatus 10 in accordance with the present invention during calibration of apparatus 10 which may involve adjustment of gap width w, cylinder rotation speed, or both, as well as adjustment of the flow rate through apparatus 10, so as to provide substantially similar or identical flow characteristics for the sample of known emulsion passed through apparatus 10 as compared with the flow characteristics obtained in the particular environment of interest. Once the flow characteristics of the emulsion through apparatus 10 substantially coincide with those determined using the actual pipeline, apparatus 10 is properly calibrated and can be used to characterize or determine the dynamic stability of other emulsions as well.

The following is an illustrative example of how apparatus 10 may be calibrated so as to represent the flow mechanisms that induce stability when an emulsion is handled by a pump.

Initially, representative values are estimated for the following parameters, based on the geometry and rotational speed of the pump and the pumping rate: maximum nominal shear rate; minimum gap size, specific energy delivered to the fluid; and ratio of area in a flow restriction inlet relative to outlet.

The rotor diameter is selected together with the rotor speed such that the maximum nominal shear rate in the gap of smallest dimension is equal that of the pump. Where a pump makes use of pressure gradients to generate flow there will be contractions and expansions (e.g. a centrifugal pump). To represent the flow in these restrictions a rotor positioned eccentric with respect to the outer cylinder is preferred. The degree of eccentricity is dictated by the need to reproduce pressure gradients of the same order as those estimated to exist in the pump.

The pressure applied to force the emulsion through the device is adjusted until the nominal residence time in the device is equal to or greater than that for the pump. Once the residence time and shear rate distribution are calculated, a check is made to see that the specific energy is of the same order as that for the pump. Small adjustments may be made to either the gap dimension, eccentricity, the rotor speed or the residence time in order to approximate all the parameters determined above, and the calibrated apparatus according to the invention can then be used to accurately represent the desired flow conditions.

It should be noted that although FIGS. 1 and 2 show apparatus 10 and system 30 including a substantially fixed external cylinder 12 and a rotatable inner cylinder 18, and wherein the external cylinder 12 is laterally movable with respect to its axis relative to inner cylinder 18, it is entirely within the scope of the present invention to provide cylinders 12, 18 wherein inner cylinder 18 is movable laterally with respect to its axis relative to external cylinder 12, and/or wherein external cylinder 12 is rotated relative to a substantially fixed inner cylinder 18.

Of course, and as shown in FIGS. 1 and 2, external cylinder 12 preferably has a diameter which is sufficiently greater than the diameter of inner cylinder 18 that a wide range of gap widths can be provided through movement of one cylinder relative to the other in accordance with the present invention. Further, a number of additional cylinders of different sizes can be used in order to further expand the versatility of apparatus 10.

Although a number of various calibration settings or positions of cylinders 12, 18 and speed of rotation one relative to the other can be provided, it is preferred that cylinders 12, 18 be positioned such that gap 22 has a width of between about 0.1 mm and about 5.0 mm, and it is further preferred that one or the other cylinders 12, 18 be rotated relative to the other cylinder at a rotational speed sufficient to expose the emulsion to shear at a rate between about 100 $s^{-1}$ and about 100,000 $s^{-1}$. Further, it has been found that testing of emulsions in accordance with the present invention is enhanced when the emulsions are heated to a temperature of between about ambient or room temperature to about 80° C.

It should be noted that apparatus 10 may be used by flowing an emulsion through gap 22 for a number of cycles until the emulsion breaks, wherein the number of cycles before breaking or phase inversion is indicative of relative dynamic stability. Alternatively, an emulsion may be flowed through gap 22 a predetermined threshold number of cycles, which could be one or more, with a subsequent evaluation of emulsion qualities such as average droplet diameter and size distribution, and changes in these qualities are directly indicative of dynamic stability of the emulsion after flow through a particular flow environment.

It should readily be appreciated that the apparatus and method of the present invention advantageously provide for an excellent degree of quality control in connection with emulsions to be provided such that emulsions of a particular type or quality are not shipped through a particular flow environment which would destroy same, and such that emulsions can be certified as having a particular quality.

It should also be understood that flow through system 30 as illustrated in FIG. 2 is controlled through a number of various valves, some of which are illustrated in FIG. 2, which valves would be well known to one of ordinary skill in the art and form no part of the present invention.

The following examples further illustrate the method and apparatus of the present invention.

EXAMPLE 1

Figure 3:
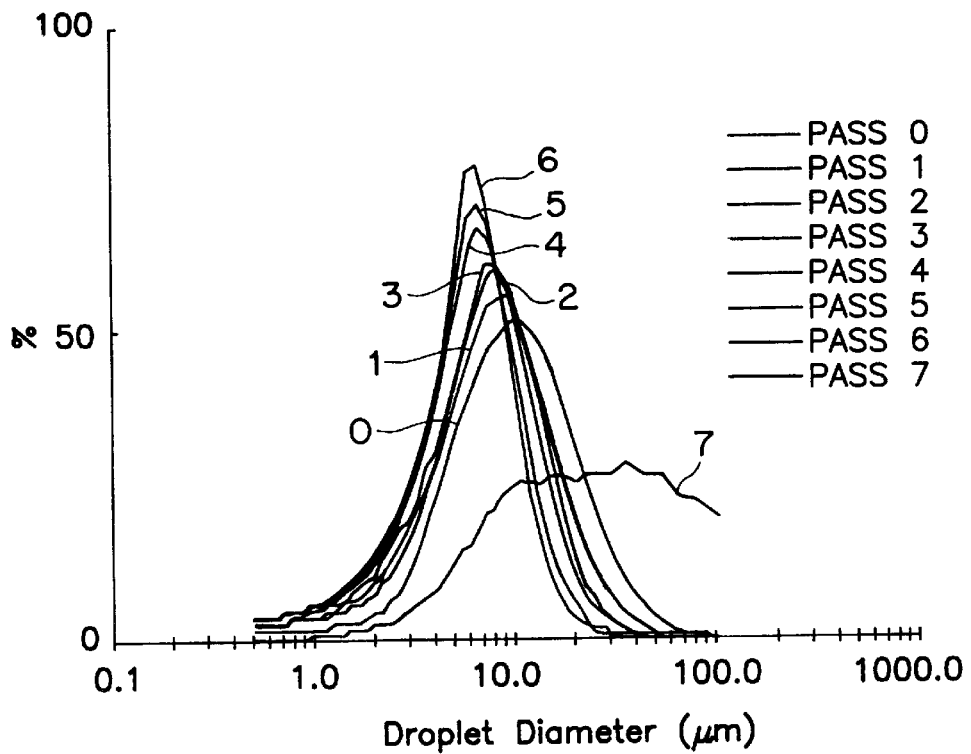
FIG. 3 illustrates the droplet size distribution for an emulsion tested over a number of passes in an apparatus in accordance with the present invention.
Figure 5:
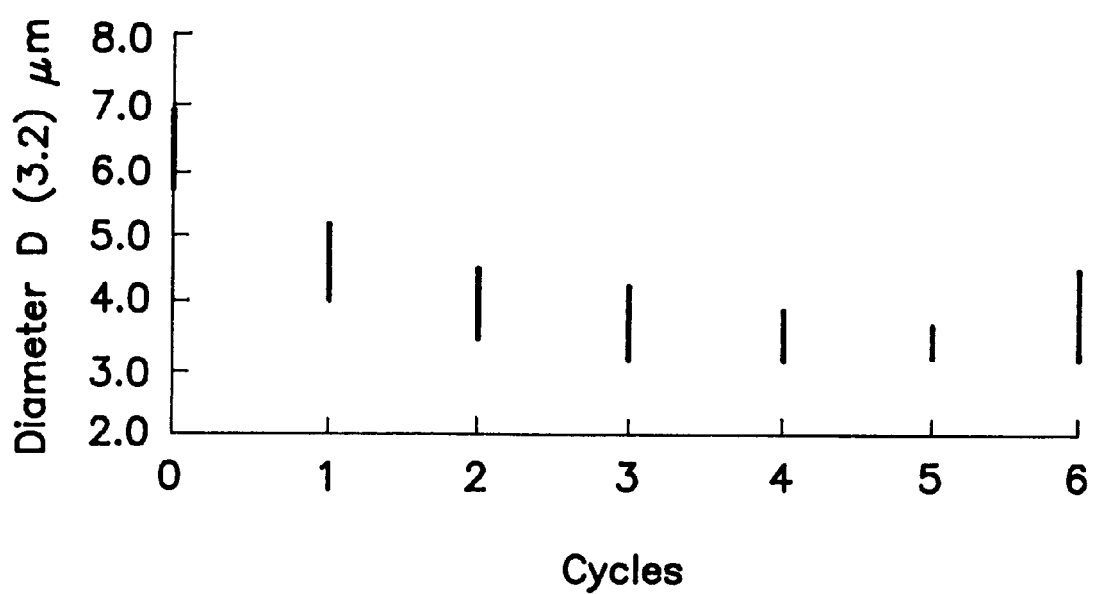
FIG. 5 illustrates the mean droplet diameter obtained for repeated tests using the same emulsion type in the apparatus and method of the present invention.

In this example, a commercial Orimulsions® bitumen in water emulsion was taken as a reference pattern for a good emulsion, and was passed through various successive cycles through apparatus 10 in accordance with the present invention using a gap width of 2 mm, rotation speed of 6500 rpm, nominal shear in gap of about 8000 $s^{-1}$, and residence time of about 3s. After each cycle, the resulting emulsion was tested so as to determine the characteristics of the emulsion, specifically droplet diameter distribution and the like. FIG. 5 shows the droplet diameter D (3,2) for a number of passes or cycles leading up to a breaking of a number of emulsions which are further discussed in Example 2. Once the emulsion was sufficiently sheared by the apparatus of the present invention, the droplet diameter D (3,2) was eventually reduced by approximately 40%, and the specific area had increased by almost 70%, and the emulsion did not tolerate further shearing which led to local phase reversal of the emulsion (seen as formation of lumps). The number of passes required until obtaining destabilizing of the emulsion together with a minimum diameter value D (3,2), referred to as the critical diameter, are parameters useful for characterizing the dynamic stability of the emulsion. Referring now to FIG. 3, the widest and lowest smooth distribution curve represents the original sample (pass 0), while the narrowest and highest distribution curve indicates the critical pass, or minimum diameter pass, which in this case was pass 6. The irregular-form distribution in FIG. 3 represents a massive coalescence of the emulsion which occurred at pass 7.

A second emulsion was prepared by flowing the emulsion through 15 passes through a two inch capillary circuit so as to provide an emulsion to be considered of lesser quality as compared to the emulsion represented in FIG. 3. This lesser quality emulsion was then passed through apparatus 10 in accordance with the present invention, and destabilization was reached after two passes. This is illustrated in FIG. 4.

Figure 4:
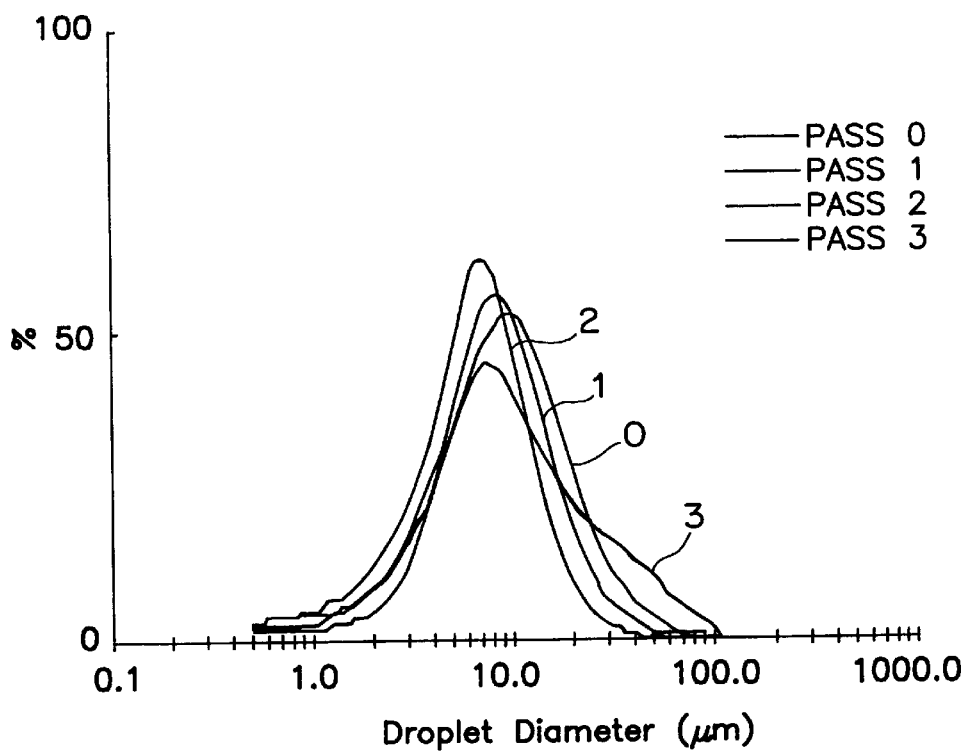
FIG. 4 illustrates the droplet size distribution for an emulsion tested over a number of passes in an apparatus in accordance with the present invention.

Based upon the results illustrated in FIGS. 3 and 4, it is clear that apparatus 10 in accordance with the present invention is capable of discriminating between emulsions of different quality.

EXAMPLE 2

In this example, a set of 15 tests were carried out using the apparatus of the present invention and commercial Orimulsionm® product from the Jose Terminal and the Morichal Plant MPE-1. Each of the 15 emulsions was passed through an apparatus in accordance with the present invention, and droplet diameter D (3,2) was measured for these samples after each cycle or pass. FIG. 5 illustrates the results of these cycles, and shows that variability of the results is greatest for the original samples, and that the apparatus has excellent repeatability, and provides reliable measurements.

As shown in FIG. 5, the number of passes before experiencing phase reversal was repeatable within 5±1 passes. This was ratified based upon 6 months use of equipment in the field. The standard deviation of results provided with the apparatus in accordance with the present invention as compared to the actual flow environment was 0.8 passes, which is within the range of apparatus resolution (1 pass). Furthermore, the critical diameter value is also repeatable, and the mean value resulted to be about 3.6 $\mu$m with a standard deviation of about 0.1 $\mu$m. The mean value of measurements of the original sample was 6.0 $\mu$m, with a deviation of 0.27 $\mu$m. In both cases, the standard deviation is small as compared to the variability in measurement using a conventional instrument (Malvern), which is of the range of approximately ±1.0 $\mu$m.

It is to be understood that the invention is not limited to the illustrations described and shown herein, which are deemed to be merely illustrative of the best modes of carrying out the invention, and which are susceptible of modification of form, size, arrangement of parts and details of operation. The invention rather is intended to encompass all such modifications which are within its spirit and scope as defined by the claims.

What is claimed is:

1. An apparatus for characterizing dynamic stability of an emulsion, comprising:
   a test vessel comprises a first cylinder having a first diameter, a second cylinder having a second diameter smaller than said first diameter, said second cylinder being positioned eccentrically within said first cylinder so as to define a gap having a width w between an outer surface of said cylinder and an inner surface of said first cylinder, and wherein one cylinder of said first and second cylinders is rotatable relative to the other cylinder of said first and second cylinders;
   means for adjusting the width w of said gap;
   means for feeding an emulsion through said gap within said test vessel; and
   means for determining the dynamic stability of said emulsion based upon cycles of flow through said test vessel.

2. An apparatus according to claim 1, further comprising means for rotating said one cylinder.

3. An apparatus according to claim 1, wherein said second cylinder is rotatable relative to said first cylinder, and further comprising means for rotating said second cylinder.

4. An apparatus according to claim 1, wherein said first and second cylinders define said gap at a narrowest point between said outer surface of said second cylinder and said inner surface of said first cylinder.

5. An apparatus according to claim 1, wherein said means for adjusting comprises means for moving one cylinder of said first and second cylinders relative to the other cylinder of said first and second cylinder.

6. An apparatus according to claim 1, wherein said first cylinder and said second cylinder each have a central axis and a cylinder surface, and wherein said central axis of said first cylinder is spaced from said central axis of said second cylinder.

7. An apparatus according to claim 1, further comprising means for a djusting a width of said gap.

8. An apparatus according to claim 7, wherein said means for adjusting comprises means for moving one surface of said stationary and moving surfaces relative to the other surface of said stationary and moving surfaces so as to adjust said width of said gap, whereby said emulsion can be characterized at different conditions.

9. An apparatus according to claim 1, wherein said means for feeding comprises an inlet arranged in said test vessel so as to introduce flow into said test vessel at said gap.

10. A method for characterizing dynamic stability of an emulsion, comprising the steps of:
    (a) providing an emulsion to be evaluated;
    (b) flowing said emulsion through a gap defined between a stationary surface and a moving surface so as to expose said emulsion to a flow field; and
    (c) repeating step (b) for a number of cycles selected from the group consisting of a first number of cycles sufficient to break said emulsion, and a preselected threshold second number of cycles, and determining the dynamic stability of the emulsion wherein said number of cycles is indicative of dynamic stability of said emulsion.

11. A method according to claim 10, wherein step (b) comprises flowing said emulsion through said gap so as to expose said emulsion to said flow field including at least one component selected from the group consisting of shear, pressure gradient and combinations thereof.

12. A method according to claim 10, wherein step (b) comprising flowing said emulsion through said gap so as to expose said emulsion to said flow field including a shear of between about 100 s$^{-1}$, and about 100,000 s$^{-1}$.

13. A method according to claim 10, wherein said step (b) comprises the steps of:
    (i) providing a test vessel having said means defining said gap within said test vessel; and
    (ii) feeding said emulsion through said gap within said test vessel; and wherein said step (c) comprises repeating step (ii) for said number of cycles.

14. A method according to claim 13, wherein said test vessel comprises a first cylinder having a first diameter, and said means defining said gap comprises a second cylinder having a second diameter smaller than said first diameter, said second cylinder being positioned eccentrically within said first cylinder so as to define said gap between an outer surface of said second cylinder and an inner surface of said first cylinder, and wherein one cylinder of said first and second cylinder is rotatable relative to the other cylinder of said first and second cylinders.

15. A method according to claim 14, wherein said first cylinder and said second cylinder each have a central axis and a cylinder surface, and wherein said central axis of said first cylinder is spaced from said central axis of said second cylinder.

16. A method according to claim 10, further comprising the step of determining an expected environment to which said emulsion will be exposed, and calibrating said means defining said gap so as to simulate said environment.

17. A method according to claim 16, further comprising the steps of:
    determining flow characteristics for a test emulsion through said environment;
    calibrating said means defining said gap so as to provide a calibrated gap providing said test emulsion with said flow characteristics for flow of said test emulsion through said calibrated gap; and
    flowing said emulsion to be characterized through said calibrated gap so as to obtain expected flow characteristics of said emulsion for flow through said environment.

18. A method according to claim 16, wherein said calibrating step comprises adjusting at least one parameter selected from the group consisting of width of said gap, speed of said moving surface, emulsion flow rate through said gap, and combinations thereof.

19. A method according to claim 18, further comprising adjusting said width of said gap between about 0.1 mm and about 5.0 mm.

20. A method according to claim 18, further comprising adjusting speed of said moving surface so as to expose said emulsion to said flow field including shear at a rate between about $100 \text{ s}^{-1}$ and about $100,000 \text{ s}^{-1}$.

21. A method according to claim 10, further comprising heating said emulsion to a temperature of between about ambient and about 80° C.

22. A method according to claim 10, wherein said emulsion comprises a viscous hydrocarbon in water emulsion.

23. A method for determining dynamic stability of an emulsion in a flow environment, comprising the steps of:

providing an emulsion;

providing a gap having a width between a stationary surface and a moving surface wherein the moving surface moves substantially perpendicularly to said width;

calibrating said width and movement speed of said moving surface so as to simulate flow conditions of said flow environment;

flowing said emulsion through said gap so as to subject said emulsion to a flow field; and determining dynamic stability of said emulsion in said flow environment by evaluating said emulsion after flow through said gap.

24. A method according to claim 23, wherein said flowing step comprises flowing said emulsion through said gap so as to expose said emulsion to said flow field including at least one component selected from the group consisting of shear, pressure gradient and mixtures thereof.

* * * * *